(12) United States Patent
Cappuzzo et al.

(10) Patent No.: US 8,899,479 B2
(45) Date of Patent: Dec. 2, 2014

(54) METHOD AND SYSTEM FOR MONITORING THE FLOW AND USAGE OF MEDICAL DEVICES

(75) Inventors: Sandro Cappuzzo, Rome (IT); Antonio Rizzi, Parma (IT); Andrea Volpi, Parma (IT)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 318 days.

(21) Appl. No.: 13/498,425

(22) PCT Filed: Sep. 28, 2009

(86) PCT No.: PCT/EP2009/062511
§ 371 (c)(1),
(2), (4) Date: May 30, 2012

(87) PCT Pub. No.: WO2011/035817
PCT Pub. Date: Mar. 31, 2011

(65) Prior Publication Data
US 2012/0234915 A1    Sep. 20, 2012

(51) Int. Cl.
*G06Q 10/06*    (2012.01)
*G06F 19/00*    (2011.01)

(52) U.S. Cl.
CPC .................................. *G06F 19/327* (2013.01)
USPC ........................................ 235/385; 705/333

(58) Field of Classification Search
CPC ....... G06Q 10/00; G06Q 90/00; G06Q 10/08; G06Q 10/087
USPC .......................................... 235/385; 705/333
See application file for complete search history.

(56) References Cited

U.S. PATENT DOCUMENTS

| 2003/0160698 | A1  | 8/2003  | Andreasson et al. |
|---|---|---|---|
| 2004/0193449 | A1  | 9/2004  | Wildman et al. |
| 2005/0091996 | A1* | 5/2005  | Ishikawa et al. ................ 62/126 |
| 2010/0262433 | A1  | 10/2010 | Kreiner et al. .................... 705/2 |
| 2010/0328048 | A1* | 12/2010 | Meli et al. ................... 340/10.42 |
| 2011/0016318 | A1* | 1/2011  | Syngkon et al. .............. 713/170 |
| 2011/0050423 | A1* | 3/2011  | Cova et al. ................. 340/572.1 |
| 2013/0204433 | A1* | 8/2013  | Gupta et al. .................. 700/239 |
| 2013/0248598 | A1* | 9/2013  | Dehnadi ....................... 235/385 |
| 2014/0028444 | A1* | 1/2014  | Volpi et al. ................... 340/10.1 |

FOREIGN PATENT DOCUMENTS

WO    WO 2006/108026 A2    10/2006

OTHER PUBLICATIONS

International Search Report dated Jan. 1, 2010; International Application No. PCT/EP2009/062511.

* cited by examiner

*Primary Examiner* — Allyson Trail

(57) ABSTRACT

A method for monitoring the flow and usage of a plurality of medical devices (4) in a hospital (2) environment, in which before shipping the medical devices (4) to a hospital (2) identification tags (17) are connected to said medical devices (4) which are detectable at a distance and contain a medical device identification code and, upon receiving the medical devices (4) in the hospital (2) store (13; 14), they are scanned to detect and store the medical device identification codes of the received medical devices (4) as entrance codes in a data base (31;28) and, when medical devices (4) leave the hospital (2) store (13;14) towards an operation theater block (9) or clinical department, they are scanned to detect and store the medical device identification codes of the medical devices (4) which left the hospital store (13; 14) as exit codes in the data base (31;28) and a medical device stock level in the hospital store (13, 14) is calculated on the basis of the previously stored medical device identification entrance codes and medical device identification exit codes.

9 Claims, 3 Drawing Sheets

METHOD AND SYSTEM FOR MONITORING THE FLOW AND USAGE OF MEDICAL DEVICES

The invention relates to the general field of supply and allocation of medical devices to hospitals and particularly to one or more operating theaters of a hospital.

Particularly, the invention relates to a method and a system for monitoring the flow (in the meaning of movement, transport and storage) and usage (in the meaning of the utilization for a specific medical operation and in the meaning of consumption) of medical devices.

Known methods and systems for monitoring the flow and usage of medical devices in hospitals comprise paper based or computer based storehouse register which are compiled and updated through manual data input. These known methods and systems have the drawback that the registered medical device consumption is not rapidly linked to the medical devise purchase department of the hospital in order to efficiently and timely replenish the hospital storehouse. Moreover, the known methods and systems for monitoring the flow and usage of medical devices in hospitals do not allow any detailed association of medical device usage (and hence cost) to specific surgical operations and/or doctors performing the operations and and/or patients undergoing the operations.

The general object of the present invention is therefore to provide a method and a system for monitoring the flow and usage of medical devices in hospital environments having features to obviate at least part of the drawbacks described in relation with the prior art.

A further object of the present invention is to provide a method and system for monitoring the flow and usage of medical devices in hospital environments which enable to associate medical device consumption to specific medical interventions and/or doctors and paramedical staff performing the interventions and/or patients undergoing such interventions.

A yet further object of the present invention is to provide a method and system for monitoring the flow and usage of medical devices in hospital environments which enable a rapid and efficient replenishment of the hospital storehouse with medical devices and general medical consumption material by an external provider. These and other objects are achieved by a system for monitoring the flow and usage of medical devices in hospital environments according to claim 1 and by a method according to claim 8. The dependent claims cover advantageous embodiments of the invention.

The details and advantages of the present invention shall be made apparent from the accompanying drawings and the description thereof, which illustrate embodiments of the invention and, together with the general description of the invention given above, and the detailed description of the invention given below, serve to explain the principles of the present invention.

Figure 1:
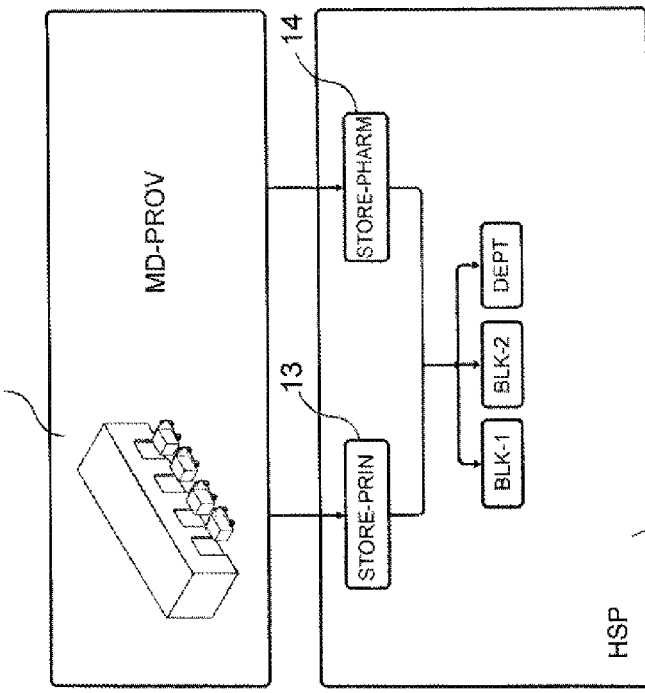
FIG. 1 illustrates schematically a macro relationship and medical device flow between a medical device supplier and a hospital.
Figure 2:
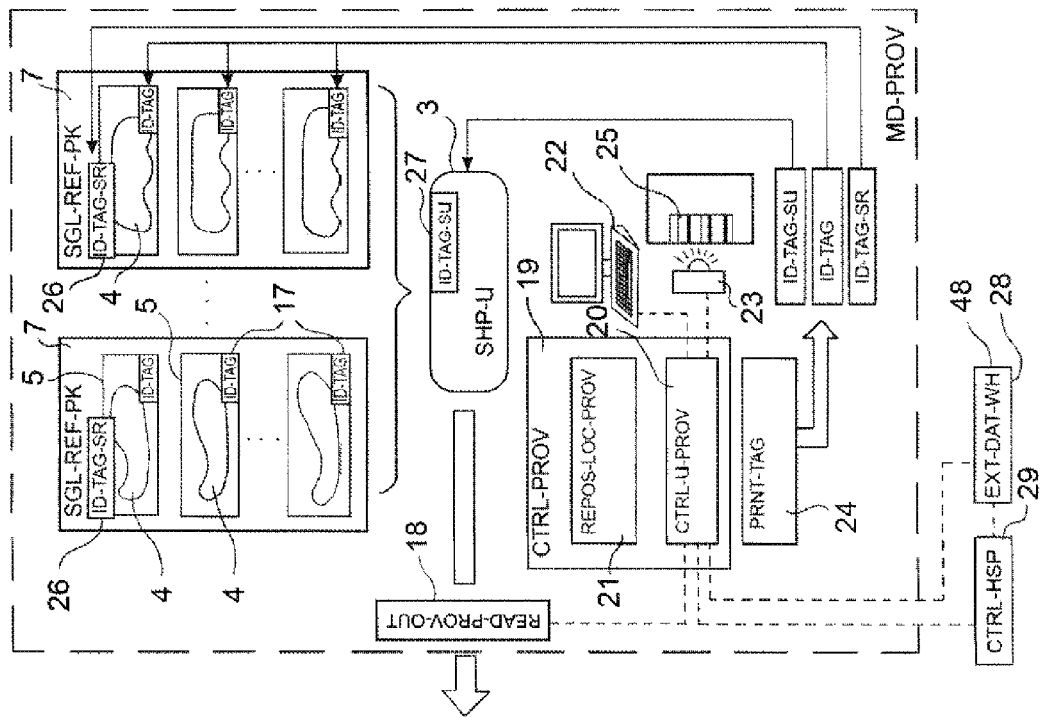
FIG. 2 is a schematic illustration of a medical device flow inside the medical device supplier's premises and the related method steps and devices of a method and system for monitoring the flow and usage of medical devices according to an embodiment of the invention.
Figure 3:
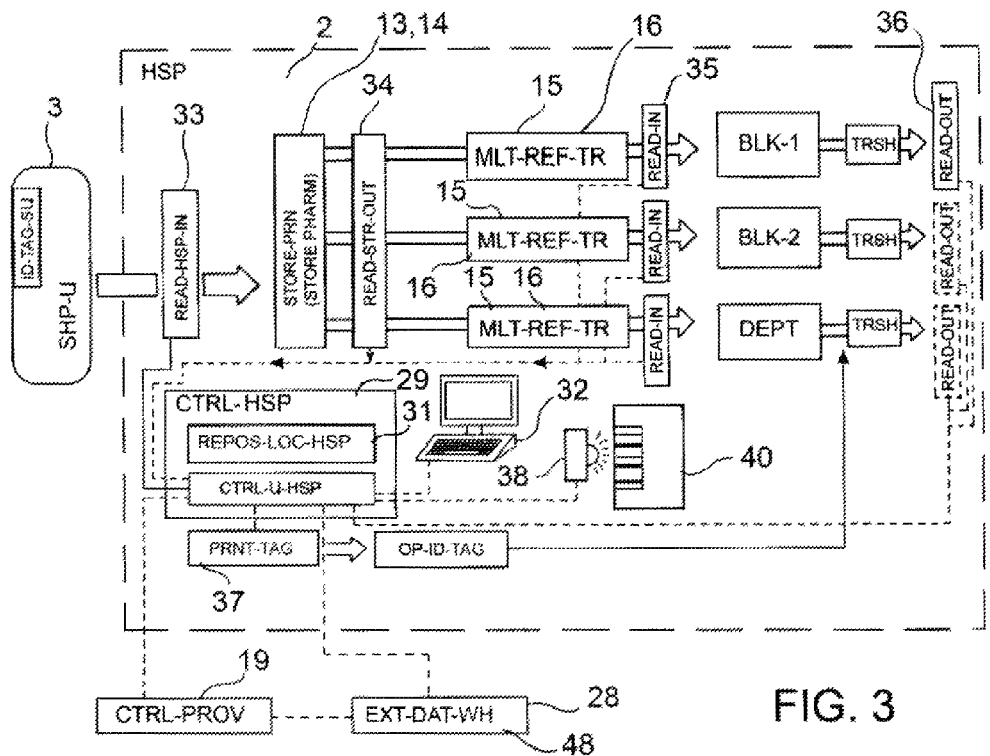
FIG. 3 is a schematic illustration of a medical device flow inside the hospital environment and the related method steps and devices of a method and system for monitoring the flow and usage of medical devices according to an embodiment of the invention.
Figure 4:
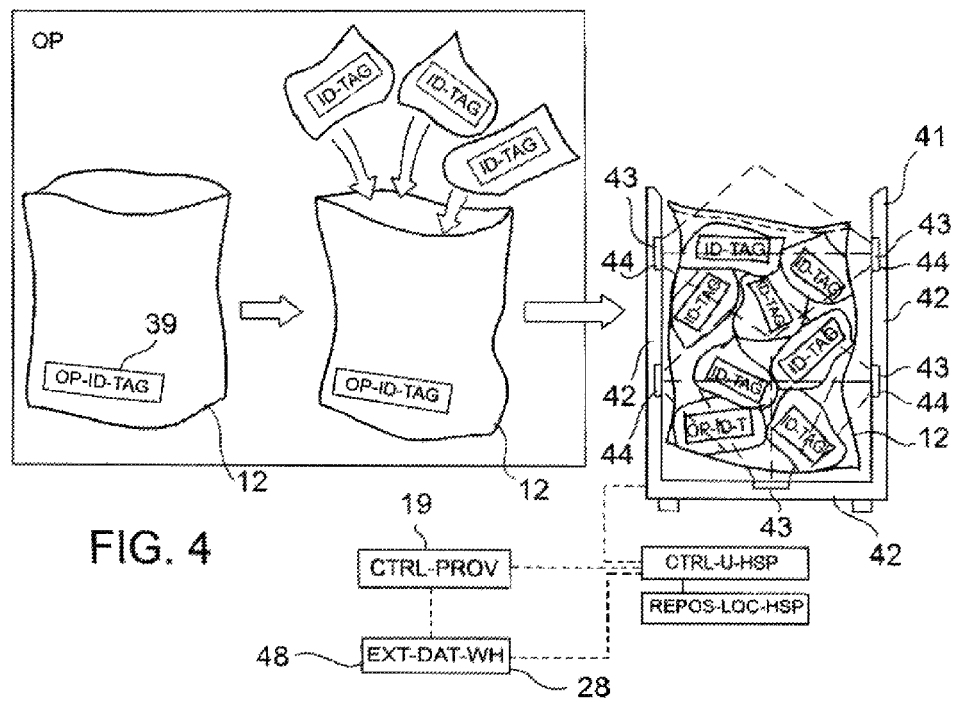
FIG. 4 is a schematic illustration of a medical device discharge flow on an operation theater level and the related method steps and devices of a method and system for monitoring the flow and usage of medical devices according to an embodiment of the invention.
Figure 5:
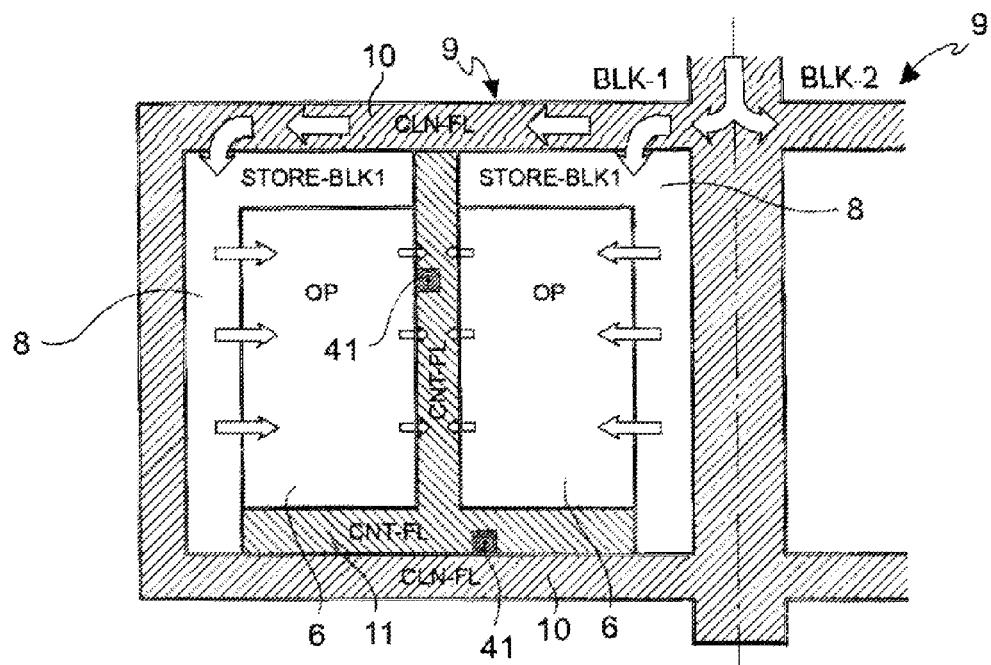
FIG. 5 is a schematic illustration of a medical device flow on an operation theater block or clinical department level and related method steps and devices of a method and system for monitoring the flow and usage of medical devices according to an embodiment of the invention.
Figures 6, 7:
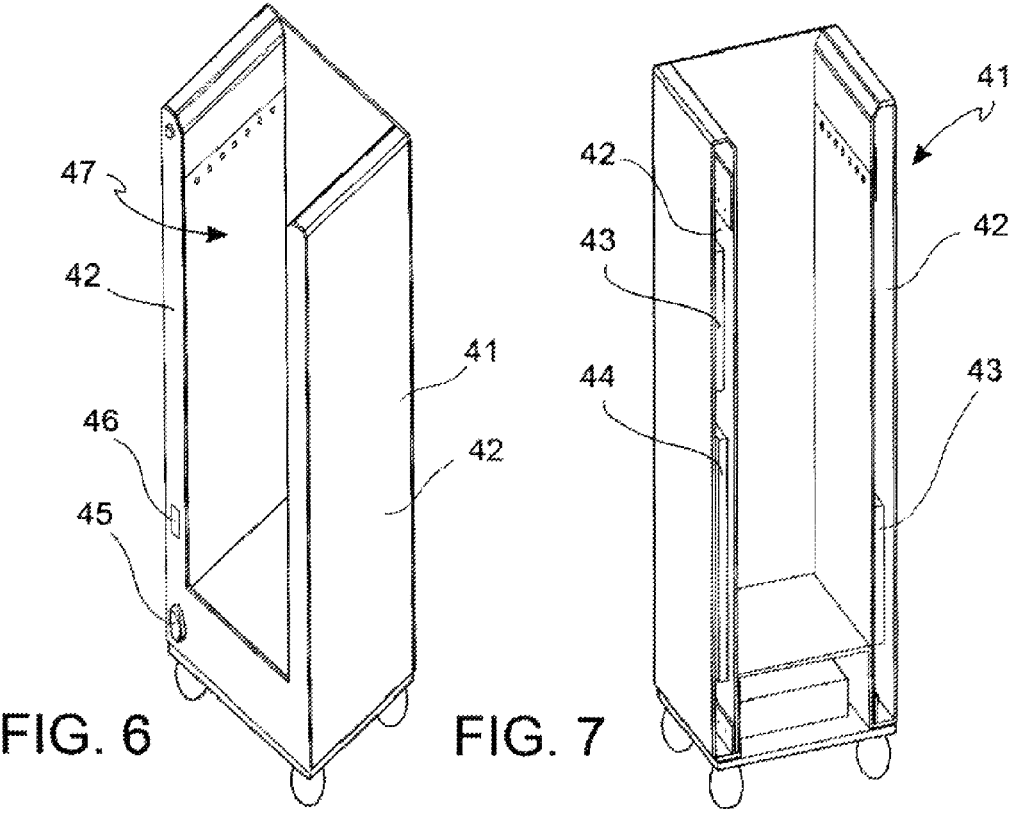
FIG. 6 is a perspective view of a medical device and operation identification data reading device in accordance with an embodiment of the invention.
FIG. 7 illustrates the ID reading device of FIG. 6 with a partially removed housing.

Turning to FIG. 1, a macro level medical device supply chain involves a medical device supplier 1 and a hospital 2 or other medical device user (customer). The medical device supplier 1 receives one or more orders from hospital 2 and prepares and ships the corresponding shipping units 3 containing the ordered medical devices 4. The hospital 2 receives, stores, uses, consumes and discharges the medical devices 4.

More specifically, in the premises of medical device supplier 1, each individual medical device 4 may be provided with a double wrapping 5 to prevent contamination in the operation theater 6 and a plurality of individual identical medical devices 4 can be united to so called single reference packages 7 which are stored and handled in the storehouse or premises of supplier 1. In dependency of the supply orders received by the hospital 2 a plurality of single reference packages 7 are grouped together to form the above said shipping units 3 which may contain different individual medical devices 4 and which are then shipped to the hospital 2.

The hospital environment may comprise a primary store 13 and a pharmacy store 14, one or more operation theater blocks 9 which can include one or more operation theaters 6 and, possibly, local medical device stores 8 associated to the operation theaters 6 and containing medical devices 4 and material intended to be used during the interventions in the operation theaters 6, clean floors 10 enabling access to the operation theaters 6 and intended to be entered only by staff and material which is not contaminated (by the patients), as well as so called black floors 11 intended to be used by contaminated hospital staff and material exiting the operation theater 6.

The shipping units 3 sent by the supplier 1 are received by the primary 13 and/or pharmacy store 14, wherein the primary store 14 may be configured as a transit point for directly forwarding the medical devices 4 and substances/medicines to the operation theater blocks 9 or other clinical departments, while the pharmacy store 14 may be configured to temporarily store the medical devices 4 and substances/medicines until they are specifically requested by the operation theater blocks 9 or other clinical departments.

In both the primary store 13 and the pharmacy store 14, the shipping units 3 are opened and the medical devices 4 are re-grouped to multi reference packages 16 and inserted in re-usable trays 15 for the transport to the operation theater blocks 9 and other clinical departments.

The multi reference packages 16 received in the operation theater block 9 are opened and the still wrapped individual medical devices 4 are stored in the local stores 8. During the interventions, the wrapping 5 of medical devices 4 as well as the contaminated and consumed medical devices 4 and organic material are put into dedicated waste bags 12 which leave the operation theater 6 through the black floor 11 towards a waste disposal room.

In accordance with an embodiment, each individual medical device 4 is provided, e.g. labeled, with an identification tag 17, preferably a passive radio frequency identification tag (passive RFID-tag), configured to be read at a distance by a handheld or stationary identification reader 18, preferably a radio frequency ID reader (RFID reader). The identification tag 17 can be connected both to the medical device 4 or to its wrapping 5.

A local supplier control unit 19, e.g. a microcomputer, comprising a CPU 20 connected with a memory containing a local supplier data repository 21 and with an interface 22 with display, keyboard and, preferably, an optical barcode reader 23, as well as an RFID printer 24 and the RFID reader 18, enables the input of the individual medical device 4 identification data (preferably: product reference code-quantity-package code-expiry date) through reading a barcode 25 provided on each individual medical device 4 package and programming and printing of the identification tags 17 which are then applied to the medical devices 4 or their wrappings 5.

The single reference packages 7 can also be provided with single reference identification tags 26, preferably also RFID-tags, and the association between the single reference package 7 ID-codes and the individual medical devices 4 ID-codes are registered in the local supplier control unit 19.

The individual medical device 4 ID codes and single reference package 7 ID-codes can be of the SGTIN (serial global identification number)-type in conformity with the standard EPCglobal.

The single reference package 7 ID-codes and the individual medical devices 4 ID-codes are saved in the local supplier data repository 21 together with supplementary data, e.g. date, hour, operator.

After the RFID labeling of the individual medical devices 4 and the single reference packages 7, the latter are grouped together and packed in the above said shipping units 3, which are also preferably labeled with a shipping unit identification tag 27, e.g. a passive radiofrequency identification tag (passive RFID tag). The shipping unit ID code can be of the SSCC (serial shipping container code)-type in conformity with the standard EPCglobal.

When the shipping unit 3 exits the medical device supplier's premises, it is scanned with the identification reader 18 which detects the shipping unit ID tag 27 and all individual ID tags 17 and single reference ID tags 26 contained therein. The local supplier control unit 19 saves the corresponding identification codes SSCC and SGTIN and their associations in the local supplier data repository 21 and, possibly, transmits these data, e.g. via internet, to an external Data Warehouse 28.

After this scanning step, the shipping unit 3 is considered send out to the hospital 2.

The hospital 2 is also provided with a local hospital control unit 29, e.g. a microcomputer, comprising a CPU 30 connected with a memory containing a local hospital data repository 31 and, possibly, with one or more interfaces 32 with display and keyboard and with:

one or more hospital store entrance identification readers 33, preferably (handheld or stationary) radiofrequency identification readers (RFID reader), configured to detect at a distance the shipping unit ID tags 27, single reference ID tags 26 and individual medical device ID tags 17 when they enter the primary store 13 or pharmacy store 14 of the hospital 2, one or more hospital store exit identification readers 34, preferably (handheld or stationary) radiofrequency identification readers (RFID reader), configured to detect at a distance the single reference ID tags 26 and individual medical device ID tags 17 contained in the trays 15 when exiting the primary or pharmacy store 13, 14 for being transported to the operation theater blocks 9 and other clinical departments, one or more hospital local store entrance identification readers 35, preferably (handheld or stationary) radiofrequency identification readers (RFID reader), configured to detect at a distance the single reference ID tags 26 and individual medical device ID tags 17 contained in the trays 15 when entering the local stores 8 associated to the operation theater blocks 9 or other clinical departments, one or more local waste exit identification readers 36, preferably radiofrequency identification readers (RFID reader), configured to detect the single reference ID tags 26 and individual medical device ID tags 17 as well as operation identification tags 39, preferably passive radiofrequency identification tags (passive RFID tag) when the used medical devices 4 and/or their wrappings 5 together with the ID tags 17 and the operation identification tag 39 exit the operation theater/s 6, preferably inside a waste bag 12.

Moreover, the local hospital control unit 29 is connected to an RFID programming device and RFID printer 37 and, preferably, to an optical barcode reader 38 configured to enable the input (through interface 32 keyboard and/or optical barcode reader 38 which can be used to scan and detect a barcode 40 applied to the patients case history file) and programming and, possibly, printing of the operation ID tags 39.

In accordance with an embodiment of the invention, when the shipping unit 3 enters the hospital 2, e.g. the primary store 13 and/or the pharmacy store 14, it is scanned with the hospital store entrance identification reader 33 which detects the shipping unit ID tag 27 and all individual ID tags 17 and single reference ID tags 26 contained therein. The local hospital control unit 29 saves the corresponding identification codes SSCC and SGTIN and their associations in the local hospital data repository 31. During this scanning step or, alternatively, upon request by the operator, the local hospital control unit 29 establishes a data connection to the local supplier control unit 19 and requests and obtains a list of the individual-, single reference-, and shipping unit identification codes of the shipping units 3 which already exited the supplier's premises and which are expected to be received by the hospital 2.

This makes it possible to visually or digitally compare the expected medical device identification data with the received medical device identification data and cross check the correctness of the delivery.

The detected and verified individual-, single reference-, and shipping unit-identification codes of the shipping units 3 received by the hospital primary or pharmacy store 3, 4 can be now transmitted, e.g. via internet using the FTP protocol, to an external Data Warehouse 28 which belongs advantageously but not necessarily to the medical device supplier 1. The data file transferred to the external Data Warehouse 28 can have the structure:

entrance;product;serial;batch;store or, alternatively:

entrance;product;quantity;batch;store.

When the trays 15 with the still wrapped medical devices 4 exit the primary store 13 and/or the pharmacy store 14 in order to be transported to the operation theater blocks 9 or clinical departments, they are scanned with the hospital store exit identification reader 34 which detects all individual ID tags 17 and, possibly, single reference ID tags 26 contained therein. The local hospital control unit 29 is configured to receive an indication (by manual data input or barcode reading etc.) of the destination of the tray 15 whose ID tags 17 are being detected and to associate the destination data to the detected product ID data. The local hospital control unit 29 saves the corresponding identification codes SGTIN and their association with the corresponding destination in the local hospital data repository 31 and can transmit them also, e.g. via internet using the FTP protocol, to the external Data Warehouse 28.

The data file transferred to the external Data Warehouse 28 can have the structure:
exit;product;serial;batch;store
or, alternatively:
exit;product;quantity;batch;store.

When the tray 15 enters the local medical device store 8 associated to an operation theater 6 or operation theater block 9 or other clinical department, it can again be scanned with the local store entrance identification reader 35 which detects all individual ID tags 17 and, possibly, all single reference ID tags 26 contained in the tray 15. The local hospital control unit 29 saves the corresponding identification codes SGTIN and their association with the corresponding local medical device store 8 in the local hospital data repository 31.

In this stage, it is possible but not necessary to transmit the locally detected medical device ID data to the external data warehouse 28.

In accordance with an embodiment of the invention, preferably before an operation and during the preparation of the operation theater 9, one or more of the above said operation identification tags 39 are programmed with an unambiguous operation identification code which can contain information identifying:
the name of the patient
the type of operation
the doctor and/or staff performing the operation
the operation theater
etc
and applied (e.g. inserted in) to the waste bag 12 or to a similar waste receiving container destined to receive the waste material of the operation identified by the operation identification tag 39.

After conclusion of the operation and insertion of the entire waste material, including the consumed medical devices 4 and wrappings 5 which still carry the individual ID tags 17, into the waste bag 12, the latter is scanned by means of the local waste exit identification reader 34 which detects all individual ID tags 17 and also the operation ID tag/s 39 contained therein or attached thereto. The local hospital control unit 29 saves the detected medical device identification data (codes SGTIN) and their association with the corresponding operation identification data in the local hospital data repository 31 and can transmit them also, e.g. via internet using the FTP protocol, to the external Data Warehouse 28.

The data file transferred to the external Data Warehouse 28 can have the structure:
exit; product; serial; batch; store; block; operation theater; operation code; doctor; patient; operation date or, alternatively:
exit; product; quantity; batch; store; block; operation theater; operation code; doctor; patient; operation date.

In accordance with an embodiment of the invention, the local waste exit identification reader 34 comprises one or more a generally box-shaped identification containers 41 suitable to completely receive the waste bag 12 and having containing walls 42 which at least partially embrace the waste bag 12 as well as a plurality of radiofrequency antennae 43 arranged at the containing walls 42 and configured to substantially cover the entire internal (waste bag receiving-) space with a radiofrequency signal adapted to stimulate the individual ID tags 17 and operation ID tag/s 39 to emit their radiofrequency identification signal, as well as one or more radiofrequency receivers 44 adapted to detect the emitted identification signals and transmit them to the local hospital control unit 29 for the above described further processing.

Preferably, the containing walls 42 of the identification container 41 define a single waste back loading aperture 47 which extends both in a frontal and top side of the identification container 41, so that the waste bag 12 can be inserted both frontally and from above.

The identification container 41 includes a remote or onboard activating switch 45 and connected signal means 46, e.g. LED, adapted to indicate the completion of the RFID detection phase ("RFID reading phase).

In accordance with an embodiment, the detection phase is concluded and accordingly indicated by the signal means 46 as a function of a preset constant time-period. Alternatively, the detection phase is concluded and accordingly indicated by the signal means 46 as a function of a preset time-period starting from the last detected different identification signal and during which no further and different identification signals are detected.

The identification container 41 can be wired or wireless connected to the hospital local control unit 29.

The obtained association between the operation identification data and the data concerning the medical devices 4 and material which has been consumed during the operation allows a focused operation cost analysis and optimization as well as a focused hospital medical device store replenishment planning and optimization.

In view of the above and in accordance with an aspect of the present invention, the method can include the step of calculating the medical device consumption and/or cost of an individual operation in dependency from the stored operation identification data and associated medical device 4 identification data.

These method steps can be performed upon request or automatically by the local hospital control unit 29 or, preferably, by an external control unit 48 which is connected to the external data warehouse 28 database and using a dedicated software.

Moreover, the method can include a step of comparing the medical device consumption and/or cost for a same type of operation performed by different doctors and/or performed using different surgical procedures/approaches and/or performed on different types of patients in dependency from the stored operation identification data and associated medical device 4 identification data. In this case, the operation identification data on the operation identification tag 39 contains also a doctor identification code and/or an approach identification code (e.g. for open surgery gastric bypass or laparoscopic gastric bypass or mixed laparoscopic—endolumenal gastric bypass) and/or a patient type identification code (e.g. male, female, obese, normal weight, age).

These method steps can also be performed upon request or automatically by the local hospital control unit 29 or, preferably, by the external control unit 48 of the external data warehouse 28.

The method may further comprise a step of generating a classification list of doctors and/or procedure types and/or medical devices listed or classified in dependency from their cost effectiveness and/or suitability for certain patient types and/or surgical procedure types on the basis of the stored operation identification data and associated medical device 4 identification data.

These method steps can also be performed upon request or automatically by the local hospital control unit 29 or, preferably, by the external control unit 48 of the external data warehouse 28.

The evaluation of the general suitability of medical devices and/or procedures would require a further data input concerning the outcome (success) of the operations and association of the operation outcome data with the stored operation identification code. This operation outcome data input and association is preferably done through the local hospital control unit 29 interface 32 with subsequent data storage in the local hospital data repository and possible data transmission to the external data warehouse 28.

The method may further comprise a step of generating a list of medical devices to be allocated for an operation type (which can be e.g. characterized by a patient type and/or a procedure type and/or a doctor), wherein said list of medical devices is calculated as a function of previously stored consumed medical device 4 identification data associated to said operation type (i.e. patient type and/or procedure type and/or doctor) and subsequently allocating the medical devices 4 for that type of operation during the preparation of the operation theater.

The generation of the medical device allocation list can also be performed upon request or automatically by the local hospital control unit 29 or by the external control unit 48 of the external data warehouse 28 and printed on paper or visualized on a display interface connected to the local hospital control unit 29.

This makes it possible to optimize the medical device 4 flow and allocation in the hospital environment.

The method may further comprise a step of selecting an operation procedure and/or a doctor and/or medical devices for a predetermined operation/disease of a predetermined type of patient on the basis of the above said classification lists derived from previously detected and stored operation identification data and medical device identification data and their association. In accordance with a further aspect of the invention, the method comprises the step of calculating a medical device stock level in the hospital primary 13 and/or pharmacy store 14 on the basis of the previously stored medical device 4 identification entrance data (read by the hospital store entrance ID reader 33) and the medical device 4 identification exit data (read by the hospital store exit ID reader 34 and/or local waste exit ID reader 36).

These method steps can be performed upon request or automatically by the local hospital control unit 29 or, preferably, by the external control unit 48 of the external data warehouse 28.

The invention further contemplates that the local hospital control unit 29 composes and transmits to the supplier 1, automatically or upon request, an order of replenishment of the hospital stores 13, 14 on the basis of the calculated medical device stock level and predetermined medical device 4 lower limit stock values. Alternatively or additionally, the external control unit 48 or the local supplier control unit 19 composes and transmits to the hospital 2, automatically or upon request, an offer of replenishment of the hospital stores 13, 14 on the basis of the calculated medical device stock level and predetermined medical device 4 lower limit stock values.

While the present invention has been illustrated by description of several embodiments and while the illustrative embodiments havebeen described in considerable detail, it is not the intention to restrict or in any way limit the scope of the appended claims to such detail. Additional advantages and modifications may readily appear to those skilled in the art.

The invention claimed is:

1. Method for monitoring the flow and usage of a plurality of medical devices (4) in a hospital (2) environment, comprising the steps of:

before shipping said plurality of medical devices (4) from a supplier (1) to a hospital (2), providing a plurality of individual medical device identification tags (17) connected to each one of said medical devices (4) and configured to provide a medical device identification information detectable at a distance and containing a medical device identification code which is unique for each of said medical devices (4) and, upon receiving said plurality of medical devices (4) in the hospital (2) store (13; 14), scanning said plurality of medical devices (4) with a hospital store entrance identification reader (36) to detect said individual medical device identification information provided by said individual medical device identification tags (12) and storing said medical device identification codes of the received medical devices (4) as entrance codes in a data base (31;28);

when medical devices (4) leave the hospital (2) store (13; 14) towards an operation theater block (9) or clinical department, scanning said medical devices (4) with a hospital store exit identification reader (34) to detect said individual medical device identification information provided by said individual medical device identification tags (12) and storing said medical device identification codes of the medical devices (4) which left the hospital store (13; 14) as exit codes in said data base (31;28);

calculating a medical device stock level in the hospital store (13, 14) on the basis of the previously stored medical device identification entrance codes and medical device identification exit codes, the method further comprising:

providing a waste bag (12) adapted to receive the medical devices (4) and medical device wrappings (5) used during an operation on a patient and, providing one or more operation identification tags (39) configured to provide an operation identification information detectable at a distance and containing an operation identification code which identifies said operation on said patient and attaching said operation identification tag (39) to said waste bag (12), scanning said waste bag (12) with a waste exit identification reader (36) to detect said operation identification information provided by said operation identification tag (39) and said individual medical device identification information provided by said individual medical device identification tags (12) inside said waste bag (12) and, receiving and associating said individual medical device identification codes and operation identification code detected from said waste bag (12) and storing said identification codes and associations in said data base (31; 28) for further elaboration.

2. Method according to claim 1, comprising the step of composing and transmitting to the supplier (1) an order of replenishment of the hospital stores (13, 14) on the basis of said calculated medical device stock level and predetermined medical device lower limit stock values.

3. Method according to claim 1 or 2, comprising the step of composing and transmitting to the hospital (2) an offer of replenishment of the hospital stores (13, 14) on the basis of the calculated medical device stock level and predetermined medical device lower limit stock values.

4. Method according to claim 1, comprising the step of calculating the medical device consumption and cost of an individual operation in dependency from the stored operation identification data and associated medical device (4) identification data.

5. Method according to claim 1 or 4, comprising the step of comparing the medical device consumption and cost for a same type of operation performed under different operating conditions in dependency from the stored operation identification data and associated medical device identification data.

6. Method according to claim 5, comprising the step of generating a classification list of operation conditions listed in dependency from said calculated cost for a same type of operation.

7. Method according to claim 6, comprising the step of selecting for a predetermined operation and disease of a predetermined type of patient an operation condition on the basis of said classification list.

8. Method according to claim 6, wherein said operation conditions are selected in the group consisting of:
- doctors who performed the operation;
- types of surgical approach used for the operation;
- types of medical devices used for the operation;
- types of patients on which the operation was performed.

9. Method according to claim 1, comprising the steps:
- generating a list of medical devices to be allocated for a specific operation type, in dependency of previously stored consumed medical device identification data associated to said specific operation type and,
- subsequently allocating the medical devices for said type of operation during the preparation of the operation theater.

* * * * *